United States Patent [19]

Schmidt et al.

[11] Patent Number: 5,753,632
[45] Date of Patent: May 19, 1998

[54] USE OF COLLOIDAL SILICA FOR THE TREATMENT OF SICKLE-CELL ANAEMIA, MALARIA AND EXOGENOUSLY INDUCED LEUCOPENIAS

[76] Inventors: Alfred Schmidt, Leinpfad 2, Hamburg, Germany, 22301; Emmanuel Bissé, Str. 19, Denzlingen, Germany, 79211; Heinrich Wieland, In der Wühre 13, St. Peter, Germany, 79271

[21] Appl. No.: 522,380

[22] PCT Filed: Apr. 5, 1994

[86] PCT No.: PCT/EP94/01056

§ 371 Date: Sep. 21, 1995

§ 102(e) Date: Sep. 21, 1995

[87] PCT Pub. No.: WO94/22456

PCT Pub. Date: Oct. 13, 1994

[30] Foreign Application Priority Data

Apr. 7, 1993 [DE] Germany ............... 43 11 546.2

[51] Int. Cl.⁶ .................................................. A01N 55/10
[52] U.S. Cl. ........................................ 514/63; 514/895
[58] Field of Search ................................ 514/63, 895

[56] References Cited

U.S. PATENT DOCUMENTS

| | | |
|---|---|---|
| 3,753,102 | 8/1973 | Beck . |
| 3,813,939 | 6/1974 | Head . |
| 3,944,354 | 3/1976 | Benwood et al. . |
| 4,179,934 | 12/1979 | Svarovsky . |
| 4,512,200 | 4/1985 | Ghering et al. . |
| 4,607,228 | 8/1986 | Reif . |
| 4,631,482 | 12/1986 | Newton et al. . |
| 4,714,890 | 12/1987 | Dechene et al. . |
| 4,904,944 | 2/1990 | Dechene et al. . |
| 5,021,426 | 6/1991 | Baldwin et al. ........... 514/313 |
| 5,022,274 | 6/1991 | Klinzing et al. . |
| 5,054,325 | 10/1991 | Dechene et al. . |
| 5,095,275 | 3/1992 | Dechene et al. . |
| 5,225,200 | 7/1993 | Gribbin ..................... 514/63 |
| 5,287,061 | 2/1994 | Dechene et al. . |
| 5,362,726 | 11/1994 | Tackie et al. ............. 514/214 |
| 5,396,806 | 3/1995 | Dechene et al. . |

FOREIGN PATENT DOCUMENTS

| | | |
|---|---|---|
| 0110802A3 | 6/1984 | European Pat. Off. . |
| A 0 126 012 | 11/1984 | European Pat. Off. . |
| 0144193A2 | 6/1985 | European Pat. Off. . |
| 0256845A2 | 2/1988 | European Pat. Off. . |
| 7402814 | 8/1974 | France . |
| 1195960 | 7/1965 | Germany . |
| 1485750 | 9/1977 | United Kingdom . |
| 1578157 | 11/1980 | United Kingdom . |
| 2121542 | 12/1983 | United Kingdom . |
| 2166874 | 5/1986 | United Kingdom . |
| WO A 82 03770 | 11/1982 | WIPO . |
| WO82/03770 | 11/1982 | WIPO ..................... 514/63 |
| WO8602453 | 4/1986 | WIPO . |
| WO8602454 | 4/1986 | WIPO . |

OTHER PUBLICATIONS

Pat. Abstract of Japan vol. 011, #173 (English Language).
(Derwent) WPIDS Abstract AN66–08545F, Aug. 31, 1993 (corresponds to DE 1171432A.).
Medline Abstract 93057493 (Heishko et al. Aug. 15, 1992).
Ivanov, Z. et al., "Peripheral blood changes induced by the chronic effect of radon and silicon dioxide (in combination or separately)", Chemical Abstracts, 83:19, Nov. 10, 1975, Abstract No.159997.

*Primary Examiner*—Keith MacMillan
*Attorney, Agent, or Firm*—Cooley Godward LLP

[57] ABSTRACT

The use of colloidal silica for the treatment of sickle-cell anaemia, malaria and exogenously induced leucopenias leads to a significant improvement in the condition of the patients.

7 Claims, No Drawings

USE OF COLLOIDAL SILICA FOR THE TREATMENT OF SICKLE-CELL ANAEMIA, MALARIA AND EXOGENOUSLY INDUCED LEUCOPENIAS

This Application is a 371 of PCT/EP94/01056, filed Apr. 5, 1994, which claims priority to German Patents P 43 11 546.2, filed Apr. 7, 1993.

Use of colloidal silica for the treatment of sickle-cell anaemia, malaria and exogenously induced leucopenias The invention relates to the use of colloidal silica for the treatment of sickle-cell anaemia, malaria and exogenously induced leucopenias.

The invention is based, inter alia, on the knowledge that the oral administration of silica in colloidal form can be employed advantageously for the treatment of homozygous patients having sickle-cell anaemia. Furthermore, the oral administration of silica causes a normalisation of the blood count, inter alia with stimulation of haematopoiesis (formation of blood).

Disorders of haematopoiesis can arise in many different ways; within the meaning of the invention these disorders are caused in particular by sickle-cell anaemia and by malaria. Exogenously induced leucopenias in particular arise as a consequence of the action of ionising radiations and as a result of treatment with medicaments such as cytostatics.

Sickle-cell anaemia is at present treated by blood transfusions. During this therapy, a haemolytic crisis occurs on average every three months. This consists, on the one hand, of a very severe intravascular haemolysis and moreover in a blockage of the arterioles and capillaries, which is very painful and leads to tissue damage in the downstream tissues. A significant disadvantage of this therapy is that the bodies of the patients are overloaded with iron. The life expectancy of the patients is about 30 years. In about half of the children, two to five haemolytic crises occur within two months.

Using the subject of the invention, it is possible in a controlled manner to decrease the total number of haemolytic crises in homozygous patients having sickle-cell anaemia; furthermore, disorders of haematopoiesis induced in other ways can also be eliminated and exogenously induced leucopenias treated.

The mechanism of action of silica in sickle-cell anaemia is not known. Inhibition of polymerisation of haemoglobin, which is abnormal in this disease, is possible. A stabilisation of the erythrocyte surface with the result that the formation of sickle cells stops and thus the haemolytic crises are avoided and the tissues are adequately perfused is furthermore also conceivable. Furthermore, an improvement in oxygen transport by the blood is also conceivable as a result of the buffer action of silicic acid, by means of which the intracellular pH of the erythrocytes is positively affected.

In a controlled investigation of patients ill with sickle-cell anaemia, it was possible by means of the use according to the invention considerably to decrease haemolytic crises occurring in the patients. 90% of the children still only had, at most, one crisis every two months; only 10% of the children suffered one crisis per month. By this means, it was possible drastically to decrease the number of necessary blood transfusions in the investigated group as well as the frequency of stays in hospital. The percentage of the children who either had to be admitted to hospital or received a blood transfusion two to three times within two months could be reduced from 20% to 0%. The use according to the invention simultaneously led to a clear decrease in the accompanying symptoms of sickle-cell anaemia. The extent of jaundice, enlargement of the spleen and osteomyelitis declined significantly during treatment.

For the investigations carried out the medicament was given in colloidal form; it contained 2.8% silica according to the invention; preparations of colloidal silica of this type are commercially available. According to the invention, the composition was given in a quantity of 2×1 tablespoons per day, dissolved or suspended in some mineral water, before meals.

The effect of the composition employed according to the invention was investigated as a function of the treatment and time, to be precise in particular with respect to 1. the number of haemolytic crises within three months and
2. the changes in the parameters of the red and white blood count.

20 children with sickle-cell anaemia were investigated. Of these, 10 untreated children served as the control group. The treated children, before they had been treated with the composition employed according to the invention, served as a further control. The age and sex distributions in the individual groups can be seen from Tables 1A and 1B.

At the start of the investigation, a differential blood count was done for each child and a clinical examination carried out in which the treatment and the number of previous haemolytic/vaso-occlusive crises were ascertained. This is shown in the left two-thirds of Table 2A.

The total examination period was 4 months. The patients were examined every 2 to 4 weeks. At the same time, the blood count parameters were determined and the number of crises and blood transfusions administered were documented.

Table 2A gives an overall view of the haemolytic/vaso-occlusive crises in the individual patient groups (control group and treated group were observed at the same time; treated group before therapy, mean values from the past two years).

Using the compositions employed according to the invention, the number of children having 4 to 5 or 2 to 3 crises per two months can be reduced from 8 or 9 to 1 child. While before therapy only 2 or 1 child had only 0 to 1 crisis every 2 months, this is now the case with 9 children. A clear decrease in the occurrence of crises thus results.

In the control group and the treated group, before the therapy according to the invention 2 to 3 transfusions per month had to be given for two or one patient. After therapy, all patients were in the group which required zero to one transfusion every 2 months; cf. Table 2B.

The frequency of the accompanying symptoms of sickle-cell anaemia, the number of blood transfusions required (L.5) and the number of haemolytic/vaso-occlusive crises (L.6) before and during use according to the invention are shown for each patient investigated in Table 3. These symptoms are: 1. icterus (L.1), 2. splenomegaly (L.2), 3. osteomyelitis (L.3), 4. infections (L.4).

The use of the composition according to the invention led to a statistically highly significant improvement in the clinical picture comprising all symptoms. It led with a 36-times increased probability to a decrease in the frequency and the intensity of the symptoms (p=0.0016).

The following legends apply to Tables 1A, 1B, 2A, 2B and 3 attached in the annexe:

Table 1A, 1B

Division of the patients according to age and sex. GE: sex; K: control group; P: treated group.

Table 2A:

Action of the composition on haemolytic/vaso-occlusive crises in the individual patient groups. AKZ2M=crises per 2 months.

Table 2B
Action of the composition on the number of blood transfusions required per 2 months (AZT2M). PO: treated group before therapy; P: after therapy.

Table 3
Overall view of the course of symptoms in the treated patients.

L.1: icterus; L.2: splenomegaly; L.3: osteomyelitis;

L.4: infections; L.5: blood transfusion (+: 2 transfusions/2 months; ++: 2-3/2 months); L.6: vaso-occlusive crises (−: none; ±0–1 crisis/2 months; +: 2–3 crises/2 months; ≧++: 4–5 crises/2 months.)

tn: time interval (n=month); −: none; ±: scarcely; +: slight, ++: moderate, +++: severe.

TABLE 1A

| age group | KP n | KP % | TP n | TP % |
|---|---|---|---|---|
| 4–10 | 6 | 60 | 6 | 60 |
| 11–20 | 3 | 30 | 2 | 20 |
| 21–30 | 1 | 10 | 1 | 10 |
| 31–40 | 0 | 0 | 1 | 10 |
| total | 10 | 100 | 10 | 100 |

TABLE 1B

| GE | K n | K % | P n | P % |
|---|---|---|---|---|
| ♀ | 5 | 50 | 3 | 30 |
| ♂ | 5 | 50 | 7 | 70 |
| total | 10 | 100 | 10 | 100 |

TABLE 2A

| AZK2M | K n | K % | PO n | PO % | P n | P % |
|---|---|---|---|---|---|---|
| 0–1 | 02 | 20 | 01 | 10 | 09 | 90 |
| 2–3 | 04 | 40 | 05 | 50 | 01 | 10 |
| 4–5 | 04 | 40 | 04 | 40 | 00 | 00 |
| total | 10 | 100 | 10 | 100 | 10 | 100 |

TABLE 2B

| AZT2M | K n | K % | PO n | PO % | P n | P % |
|---|---|---|---|---|---|---|
| 0 | 0 | 00 | 0 | 00 | 8 | 80 |
| 1 | 0 | 00 | 1 | 10 | 2 | 20 |
| 2 | 8 | 80 | 8 | 80 | 0 | 00 |
| 2–3 | 2 | 20 | 1 | 10 | 0 | 00 |
| total | 10 | 100 | 10 | 100 | 10 | 100 |

TABLE 3

| P | V1 $t_0$ | V1 $t_1$ | V1 $t_2$ | V1 $t_3$ | V2 $t_0$ | V2 $t_1$ | V2 $t_2$ | V2 $t_3$ | V3 $t_0$ | V3 $t_1$ | V3 $t_2$ | V3 $t_3$ | V4 $t_0$ | V4 $t_1$ | V4 $t_2$ | V4 $t_3$ | V5 $t_0$ | V5 $t_1$ | V5 $t_2$ | V5 $t_3$ | V6 $t_0$ | V6 $t_1$ | V6 $t_2$ | V6 $t_3$ |
|---|---|---|---|---|---|---|---|---|---|---|---|---|---|---|---|---|---|---|---|---|---|---|---|---|
| 01 | 2+ | 1+ | + | ± | + | + | ± | − | + | ± | − | − | ++ | ++ | + | + | + | − | − | − | +++ | ++ | − | − |
| 02 | 2+ | 1+ | + | ± | + | + | ± | − | + | ± | − | − | + | + | + | ± | ± | − | − | − | ± | − | − | − |
| 03 | ± | − | − | − | − | − | − | − | − | − | − | − | ± | ± | ± | − | + | − | − | − | + | ± | ± | − |
| 04 | 4+ | 3+ | 2+ | ± | ++ | + | + | + | + | + | ± | − | ++ | ++ | ++ | + | ++ | ± | − | − | +++ | ++ | + | + |
| 05 | 1+ | ± | − | − | + | ± | − | − | − | − | − | − | + | + | ± | ± | + | − | − | − | ++ | ± | ± | − |
| 06 | ± | − | − | − | − | − | − | − | − | − | − | − | + | + | ± | ± | + | − | − | − | + | − | − | − |
| 07 | 2+ | + | + | + | ++ | + | ± | ± | ++ | + | ± | ± | ++ | ++ | ++ | + | + | − | − | − | +++ | ++ | − | ± |
| 08 | − | − | − | − | − | − | − | − | + | ± | − | − | ± | − | − | − | + | − | − | − | + | − | − | − |
| 09 | 2+ | + | + | + | − | − | − | − | − | − | − | − | ± | ± | − | ± | + | − | − | − | + | ± | ± | − |
| 10 | − | − | − | − | − | − | − | − | − | − | − | − | ± | ± | − | − | + | − | − | − | + | − | − | − |

We claim:

1. A method of treating sickle-cell anemia, comprising:
   administering a therapeutically effective amount of colloidal silica to a patient in need thereof.

2. The method of claim 1, wherein said colloidal silica is administered orally.

3. A method of treating an exogenously induced leucopenia, consisting essentially of:
   administering a therapeutically effective amount of colloidal silica to a patient in need thereof.

4. The method of claim 3, wherein said leucopenia is induced by ionizing radiation or by medicaments.

5. The method of claim 3, wherein said colloidal silica is administered orally.

6. A method of treating malaria, consisting essentially of:
   administering a therapeutically effective amount of colloidal silica to a patient in need thereof.

7. The method of claim 6, wherein said colloidal silica is administered orally.

* * * * *